United States Patent
Kim et al.

(10) Patent No.: US 10,186,062 B2
(45) Date of Patent: Jan. 22, 2019

(54) CONTOUR SEGMENTATION APPARATUS AND METHOD BASED ON USER INTERACTION

(71) Applicant: Samsung Electronics Co., Ltd., Suwon-si (KR)

(72) Inventors: Ye-Hoon Kim, Seoul (KR); Kyoung-Gu Woo, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 127 days.

(21) Appl. No.: 14/058,645

(22) Filed: Oct. 21, 2013

(65) Prior Publication Data
US 2014/0146076 A1 May 29, 2014

(30) Foreign Application Priority Data
Nov. 27, 2012 (KR) .................... 10-2012-0135473

(51) Int. Cl.
G06T 11/60 (2006.01)
G06T 7/12 (2017.01)
G06F 3/0484 (2013.01)
A61B 6/00 (2006.01)

(52) U.S. Cl.
CPC .............. *G06T 11/60* (2013.01); *A61B 6/469* (2013.01); *G06F 3/04845* (2013.01); *G06T 7/12* (2017.01); *G06T 2207/20096* (2013.01)

(58) Field of Classification Search
CPC ....................................................... G06T 11/60
USPC ....................................................... 345/619
See application file for complete search history.

(56) References Cited

U.S. PATENT DOCUMENTS

| | | | |
|---|---|---|---|
| 6,560,476 B1 * | 5/2003 | Pelletier | G06T 7/0012 382/130 |
| 6,970,587 B1 | 11/2005 | Rogers | |
| 7,197,181 B1 * | 3/2007 | Cote | 382/164 |
| 7,308,126 B2 | 12/2007 | Rogers et al. | |
| 7,783,094 B2 | 8/2010 | Collins et al. | |
| 8,051,386 B2 | 11/2011 | Rosander et al. | |
| 8,214,756 B2 * | 7/2012 | Salazar-Ferrer et al. | 715/765 |
| 2006/0177133 A1 * | 8/2006 | Kee | 382/173 |
| 2007/0092124 A1 * | 4/2007 | Moriya | 382/128 |

(Continued)

FOREIGN PATENT DOCUMENTS

| | | |
|---|---|---|
| JP | 2001-54520 A | 2/2001 |
| JP | 2005-95376 A | 4/2005 |

(Continued)

OTHER PUBLICATIONS

Elder et. al., Image Editing in the Contour Domain, IEEE Transactions on Pattern Analysis and Machine Intelligence, vol. 23, No. 3, Mar. 2001.*

(Continued)

*Primary Examiner* — Hai Tao Sun
(74) *Attorney, Agent, or Firm* — Jefferson IP Law, LLP

(57) ABSTRACT

An apparatus includes an interface unit configured to provide, to a terminal, an interface supporting one or more modes, and display, on the interface, an image including a contour of a region of interest. The apparatus further includes a contour modification unit configured to modify the contour based on a mode selected by a user from the one or more modes, and an operation performed by the user.

20 Claims, 11 Drawing Sheets

(56) References Cited

U.S. PATENT DOCUMENTS

| | | | |
|---|---|---|---|
| 2007/0110291 A1 | 5/2007 | Ahn et al. | |
| 2008/0208047 A1 | 8/2008 | Delso | |
| 2008/0240553 A1* | 10/2008 | Tamai | G06K 9/2081 382/162 |
| 2008/0281182 A1 | 11/2008 | Rabben et al. | |
| 2009/0034812 A1* | 2/2009 | Nowinski et al. | 382/131 |
| 2010/0020221 A1* | 1/2010 | Tupman | G06F 3/04883 348/333.01 |
| 2011/0145759 A1* | 6/2011 | Leffert | G06F 3/04845 715/800 |
| 2011/0210850 A1* | 9/2011 | Tran | G06F 3/04883 340/540 |
| 2011/0271215 A1* | 11/2011 | Piper | 715/764 |

FOREIGN PATENT DOCUMENTS

| | | |
|---|---|---|
| KR | 10-2007-0047007 A | 5/2007 |
| WO | 2006/056614 A1 | 6/2006 |

OTHER PUBLICATIONS

Kass et al., "Snakes: Active contour model," International Journal of Computer Vision, vol. 1, (1988): pp. 321-331.

Osher et al. "Fronts propagating with curvature dependent speed: algorithms based on Hamilton-Jacobi formulation." Journal of Computational Physics 79.1 (1988): 12-49.

Chan et al. "Active contours without edges." Image Processing, IEEE Transactions on 10.2 (2001):pp. 266-277.

Gouze et al. "Interactive breast cancer segmentation based on relevance feedback: from user-centered design to evaluation." SPIE Medical Imaging. International Society for Optics and Photonics, (2009):pp. 726021-1-726021-10.

Kang; "Interactive 3D editing tools for image segmentation"; Jul. 3, 2003; Institute of /o.1edical Physics, University of Erlangen-Numherg, Kraukenlwusslr. 12, Erla11ge11 91054, Germany; XP-002607361.

\* cited by examiner

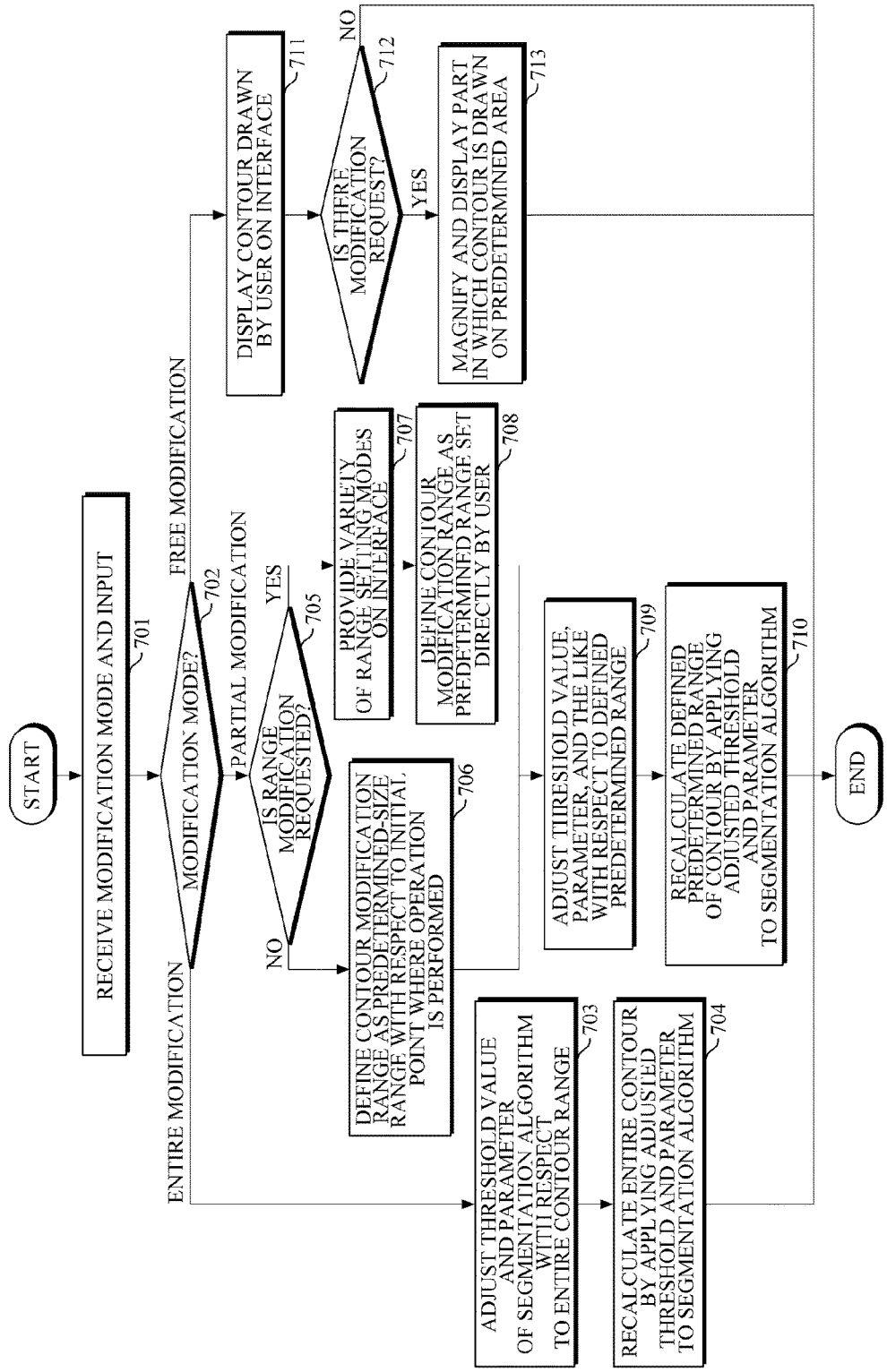

CONTOUR SEGMENTATION APPARATUS AND METHOD BASED ON USER INTERACTION

CROSS-REFERENCE TO RELATED APPLICATION

This application claims the benefit under 35 119(a) of Korean Patent Application No. 10-2012-0135473, filed on Nov. 27, 2012, in the Korean Intellectual Property Office, the entire disclosure of which is incorporated herein by reference for all purposes.

BACKGROUND

1. Field

The following description relates to an apparatus and method for segmenting a contour of a lesion region in an image based on user interaction.

2. Description of the Related Art

In general, an accurate contour of a region of interest (ROI) in a medical image may play an important role in determining diagnostic results by a computer-aided diagnosis (CAD) system. That is, when an accurate contour of an ROI, particularly, a lesion region, is obtained, a corresponding feature value for the contour may be accurately extracted. Therefore, an accurate classification about whether a corresponding lesion is benign or malignant may be made possible using the extracted feature value, thereby improving the accuracy of diagnosis.

However, since boundaries provided in a general CAD system are not always accurate, user modification is required. However, contour modification provided in the general CAD system is generally performed by inputting a point through a mouse or a touchscreen, which is inconvenient and time-consuming.

SUMMARY

In one general aspect, an apparatus includes an interface unit configured to provide, to a terminal, an interface supporting one or more modes, and display, on the interface, an image including a contour of a region of interest. The apparatus further includes a contour modification unit configured to modify the contour based on a mode selected by a user from the one or more modes, and an operation performed by the user.

In another general aspect, a method includes providing, to a terminal, an interface supporting one or more modes, and displaying, on the interface, an image including a contour of a region of interest. The method further includes modifying the contour based on a mode selected by a user from the one or more modes, and an operation performed by the user.

Other features and aspects will be apparent from the following detailed description, the drawings, and the claims.

BRIEF DESCRIPTION OF THE DRAWINGS

FIG. 7 is a detailed flowchart illustrating an example of modifying of a contour in a contour segmentation method.

DETAILED DESCRIPTION

Figure 1:
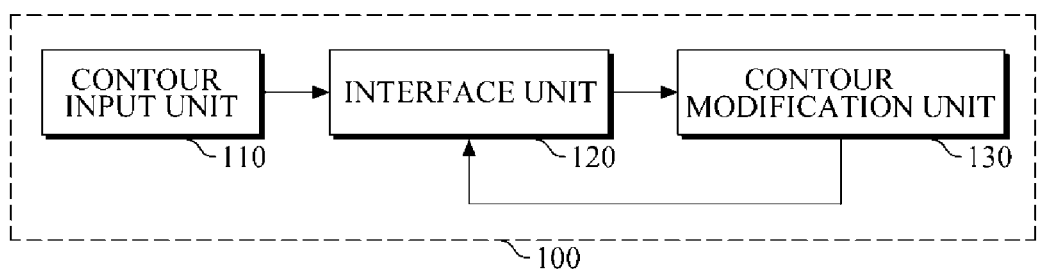
FIG. 1 is a block diagram illustrating an example of a contour segmentation apparatus.

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. Also, descriptions of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

FIG. 1 is a block diagram illustrating an example of a contour segmentation apparatus 100. The contour segmentation apparatus 100 may be applied to a computer-aided diagnosis (CAD) system, and may provide an interface so that a contour of a region of interest (ROI) (e.g., a lesion region), which is extracted from a medical image by the CAD system, may be easily and accurately modified by a user, thereby improving an accuracy of diagnosis. In addition, the contour segmentation apparatus 100 may be applied to an image processing system other than the CAD system, and may provide support to enable accurate segmentation of a contour of an ROI extracted from an image by the image processing system. Referring to FIG. 1, the contour segmentation apparatus 100 includes a contour input unit 110, an interface unit 120, and a contour modification unit 130.

The contour input unit 110 receives an image, and may receive information of a contour of an ROI extracted from the image. For example, the contour input unit 110 may receive a medical image and information of a contour of an ROI extracted from the medical image by the CAD system. In another example, the contour input unit 110 receives an image, and may apply a contour segmentation algorithm, such as, for example, an active contour model, to the received image to extract a contour of an ROI from the received image.

The interface unit 120 provides a user interactive-based interface to a user terminal. For example, the user terminal may be all hardware devices, such as a computer, a laptop, a smartphone, a tablet personal computer (PC), and/or other hardware devices known to one of ordinary skill in the art. The interface unit 120 may output the interface to a display unit (for example, a monitor, a touch panel, and/or other display units known to one of ordinary skill in the art) of the user terminal. The user may readily perform a variety of operations of modifying the contour through the provided interface, and the contour segmentation apparatus 100 may receive and process a user input corresponding to the variety of operations performed by the user. In addition, the interface unit 120 generates a contour based on the received or extracted contour, and superimposes the generated contour on the received image to display the superimposed contour on the interface.

Figure 2:
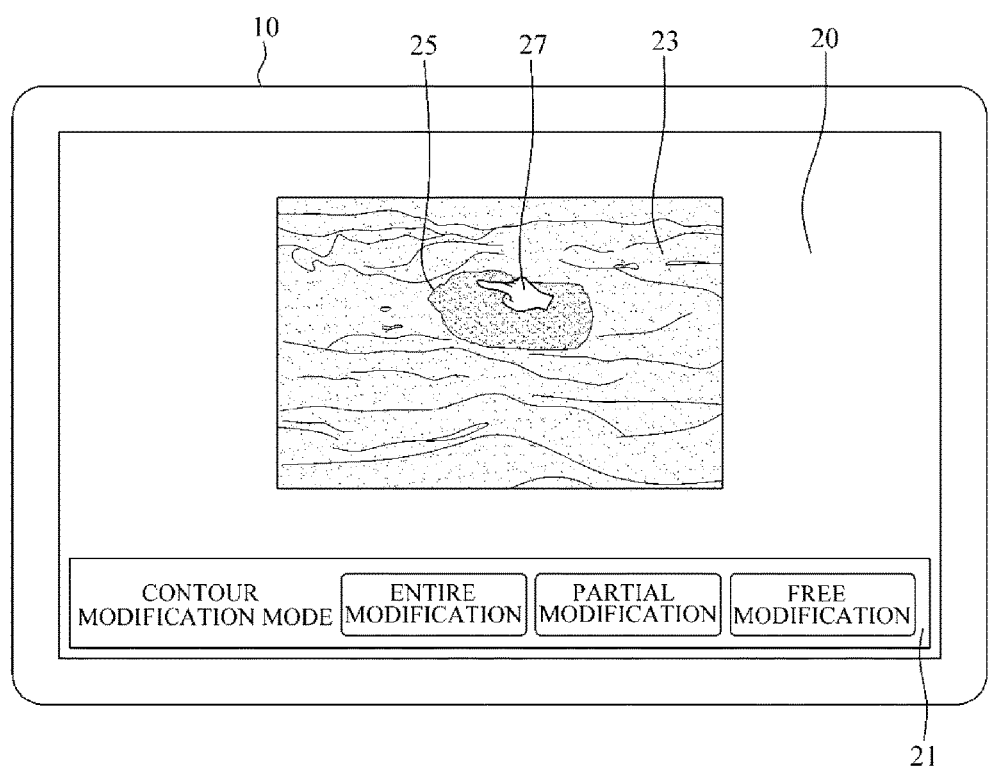
FIG. 2 is a diagram illustrating an example of an interface of a contour segmentation apparatus.

FIG. 2 is a diagram illustrating an example of an interface 20 of a contour segmentation apparatus. The interface 20 and contour modification through the interface 20 will be described with reference to FIGS. 1 and 2.

The interface unit 120 may output the interface 20 to a display unit of a user terminal 10. The interface 20 includes an image output area 23 that displays a contour 25, and a contour modification mode selection area 21 that may be used by the user to select a contour modification mode, namely, an entire modification mode, a partial modification mode, or a free modification mode. Further, the user may perform a predetermined operation in the image output area 23, using an input object 27, such as, for example, a hand, fingers, a mouse, a stylus, and/or other input objects known to one of ordinary skill in the art, to thereby modify the contour 25.

For example, the user may modify the contour 25 by repeatedly performing a click operation several times, performing a drag operation using the input object 27, and/or performing a panning operation in which movement on a touch panel in a predetermined direction is carried out. Alternatively, the user may modify the contour 25 by performing a pressing operation for a predetermined time. These operations are merely examples to which the examples of FIGS. 1 and 2 are not limited, and the contour 25 may be modified through a variety of other gestures set in advance or a multi-touch.

When the user performs a predetermined operation through the input object 27 on the interface 20, the contour modification unit 130 receives a user input corresponding to the predetermined operation, and modifies the contour 25 based on the user input and the mode selected by the user. For example, the contour modification unit 130 may modify the contour 25 inward when the user performs the predetermined operation inside the contour 25, for example, when a point (for example, a click point or a start point of a panning or dragging operation) where the user initially performs the operation is present inside the contour 25. In another example, the contour modification unit 130 may modify the contour 25 outward when the user performs the predetermined operation outside the contour 25, for example, when the point (for example, a start point of the panning or dragging operation) where the user initially performs the operation is present outside the contour 25. In still another example, when the user performs a multi-operation, the contour modification unit 130 may modify the contour 25 outward when two fingers of the user are moved toward one another while simultaneously touching the touch panel, and may modify the contour 25 inward when the two fingers are moved apart from one another while simultaneously touching the touch panel.

The contour modification unit 130 may set a threshold value of the contour segmentation algorithm to be higher than an original threshold value to thereby reduce the contour 25 when the input corresponding to the operation performed by the user is to modify the contour 25 inward. The contour modification unit 130 may set the threshold value to be lower than the original threshold value to thereby increase the contour 25 when the input is to modify the contour 25 outward.

The contour modification unit 130 may adjust the threshold value of the contour segmentation algorithm based on a type of the input corresponding to the operation performed by the user, a strength of the input, and/or a speed of the input. The contour modification unit 130 may apply the adjusted threshold value to the contour segmentation algorithm to modify the contour 25.

For example, when the operation performed by the user is an operation of generating a discrete input, such as a click operation repeated several times, a panning operation, and/or a dragging operation, an adjustment width of the threshold value may be relatively increased to recalculate the contour 25, whereby it may appear that the contour 25 is discretely changed. When the operation performed by the user is an operation of generating a continuous input, such as a pressing operation for a predetermined time, the adjustment width of the threshold value may be relatively reduced to recalculate the contour 25, whereby it may appear that the contour 25 is continuously changed.

In another example, the adjustment width of the threshold value may be adjusted more minutely based on the speed of the input. For example, when a speed of a click operation is increased while the click operation is repeated by the user several times, the adjustment width of the threshold value may be relatively reduced, and when the speed of the click operation is reduced while the click operation is repeated by the user several times, the adjustment width of the threshold value may be relatively increased, thereby adjusting a degree of a change in the contour 25. In the same manner, when a speed of a panning operation performed by the user is increased or reduced, the adjustment width of the threshold value may be relatively increased or reduced, thereby adjusting the degree of the change in the contour 25.

In still another example, it is possible to adjust the degree of the change in the contour 25 by more minutely adjusting the adjustment width of the threshold value based on the strength of the input. For example, when a pressure or input strength of a pressing operation is increased while the user performs the pressing operation for a predetermined time, the adjustment width of the threshold value may be relatively reduced so that the contour 25 may be more continuously changed. When the input strength of the pressing operation is reduced while the user performs the pressing operation for a predetermined time, the adjustment width of the threshold value may be relatively increased so that the contour 25 may be relatively discretely changed.

In yet another example, when a pressing operation for a predetermined time is performed by the user, the contour modification unit 130 may set a time unit in advance, and may change the adjustment width of the threshold value whenever the set time unit has elapsed, thereby adjusting the threshold value. For example, the adjustment width of the threshold value may be reduced whenever a pressing time has elapsed in a unit of three seconds, so that a changed width of the contour 25 may be reduced.

When the contour 25 is recalculated by the contour modification unit 130, the interface unit 120 generates the recalculated contour 25, and displays the generated contour 25 on the interface 20. When the contour 25 is repeatedly modified by the contour modification unit 130, the interface unit 120 repeatedly displays a change in the modified contour 25 on the interface 20, so that the user may confirm the contour 25 changed based on the operation the user has performed.

In this example, the interface unit 120 may display the change in the contour 25 on the interface 20 by differentiating a type, a color, and/or a thickness of the contour 25 from those of an original contour, so that the user may easily confirm the change in the contour 25 with the naked eye. For example, when the original contour is a black solid line, the modified contour 25 may be displayed in a variety of combinations, such as a black dotted line, a red solid line, and a red dotted line.

Meanwhile, the user may select a contour modification mode from the contour modification mode selection area 21 of the interface 20 that is used to modify the contour 25. Hereinafter, contour modification modes will be described with reference to FIGS. 3A to 5B.

Figure 3A:
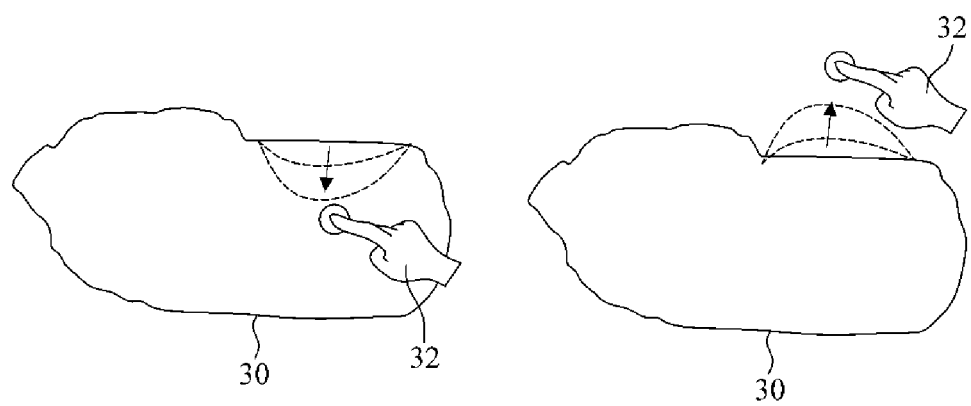
FIGS. 3A to 3D are diagrams illustrating examples of a partial modification mode of a contour segmentation apparatus.

FIGS. 3A to 3D are diagrams illustrating examples of a partial modification mode of the contour segmentation apparatus 100. FIG. 3A is a diagram illustrating an example in which a contour 30 is modified in a partial modification mode, and as shown in FIG. 3A, a part or predetermined range of the contour 30 is modified. A left side of FIG. 3A shows that the contour 30 is modified inward by the user operating an input object 32 inside the contour 30 on an interface, and a right side of FIG. 3A shows that the contour 30 is modified outward by the user operating the input object 32 outside the contour 30 on the interface.

Figure 3B:
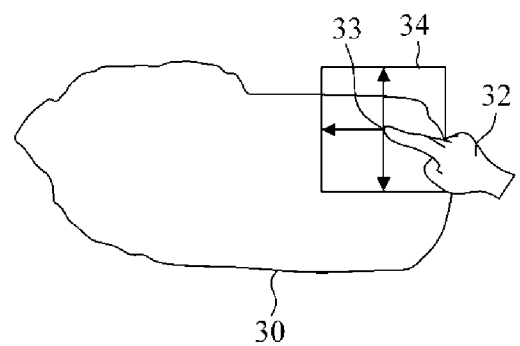

Referring to FIGS. 1 and 3B, when the user selects the partial modification mode among the contour modification modes, the contour modification unit 130 may partially modify the contour 30 by applying a contour segmentation algorithm to the predetermined range of the contour 30. The predetermined range may be a range 34 set in advance with respect to an initial point 33 where the user performs an operation through the input object 32. When the range 34 is set to be increased so as to include the entire contour 30, an entire modification mode may be operated even though the user selects the partial modification mode, and therefore, the contour segmentation algorithm may be applied to an entire range of the contour 30.

Figure 3C:
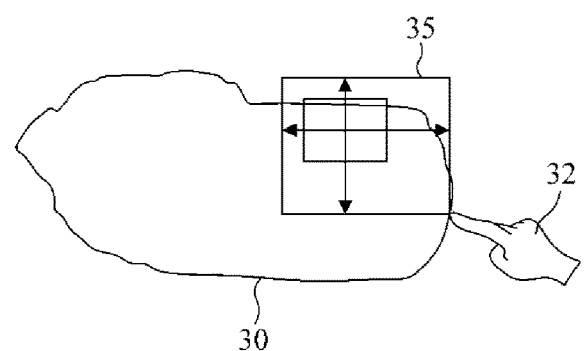
Figure 3C:
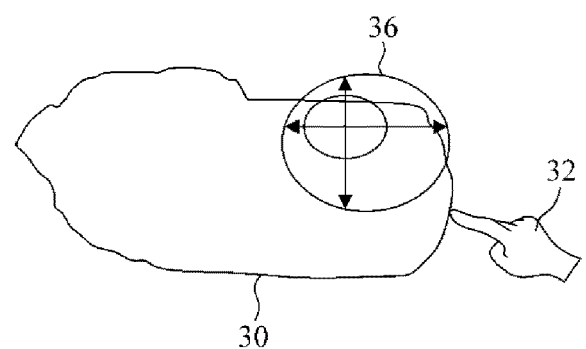
Figure 3D:
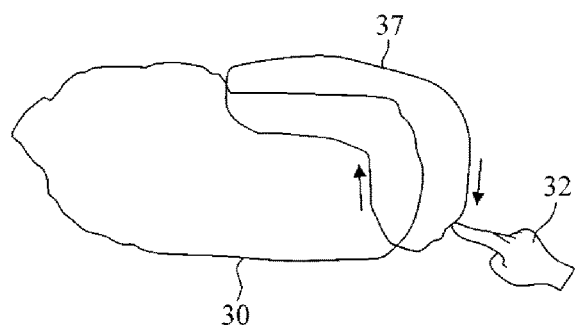
Figure 3D:
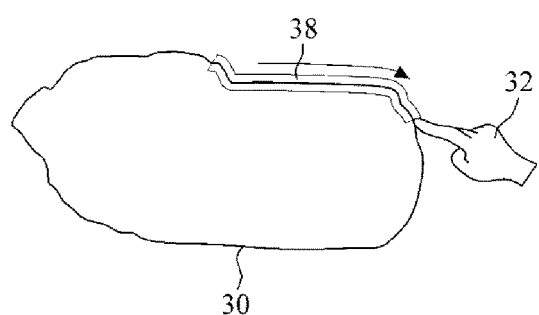

In addition, the user may directly set the predetermined range to which the contour segmentation algorithm is applied, as shown in FIGS. 3C and 3D. Referring to FIGS. 1 and 3C, the interface unit 120 outputs, on the interface, FIGS. 35 and 36, respectively, including respective predetermined shapes (for example, a circle, ellipse, polygon, and/or other shapes known to one of ordinary skill in the art) designated or selected by the user when the user selects the partial modification mode. The user may adjust sizes of the respective FIGS. 35 and 36, using the input object 32, whereby the predetermined range of the contour 30 is set to correspond to the FIG. 35 or 36.

In addition, as shown in an upper portion of FIG. 3D, the user may designate a free region 37 through the input object 32 to modify a part of the contour 30 that corresponds to the free region 37, whereby the predetermined range of the contour 30 is set to correspond to the free region 37. In addition, as shown in a lower portion of FIG. 3D, the user may select the predetermined range of the contour 30 in the form of a free curved line 38, using the input object 32, whereby the predetermined range is set to correspond to the free curved line 38.

Referring again to FIGS. 1 and 3C to 3D, when the user selects the partial modification mode, the interface unit 120 may output, on the interface, a menu (for example, a popup menu)) that may be used by the user to select a method of setting a modified range of the contour 30 (for example, through figures, a free region, and a free curved line). When the user selects to a method of setting the modified range through the figures, the interface unit 120 may output, on the interface, an additional menu that may be used by the user to select any one of a variety of figures. When the user sets the predetermined range to be used to modify the contour 30 to include the entire contour 30, the entire modification mode may be operated, and the contour segmentation algorithm may be applied to the entire contour 30.

Figure 4:
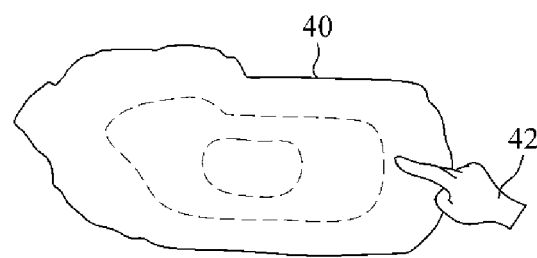
FIG. 4 is a diagram illustrating an example of an entire modification mode of a contour segmentation apparatus.
Figure 4:
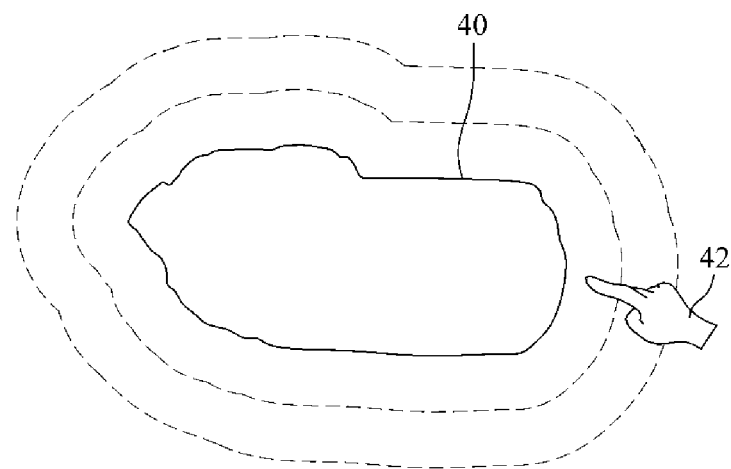

FIG. 4 is a diagram illustrating an example of an entire modification mode of the contour segmentation apparatus 100. Referring to FIGS. 1 and 4, when a user selects the entire modification mode among contour modification modes of an interface, the contour modification unit 130 adjusts a threshold value of an entire range of a contour 40 based on an input corresponding to an operation performed by the user to thereby apply the contour segmentation algorithm to the entire range and recalculate the contour 40.

In more detail, as shown in an upper portion of FIG. 4, when the user performs a predetermined operation, such as, for example, a click operation, through an input object 42 inside the contour 40, the contour modification unit 130 adjusts the threshold value to be higher than an original threshold value, so that the contour 40 is modified inward, that is, in a direction in which the contour 40 is reduced. Alternatively, as shown in a lower portion of FIG. 4, when the user performs a predetermined operation through the input object 42 outside the contour 40, the contour modification unit 130 adjusts the threshold value to be lower than the original threshold value, so that the contour 40 is modified outward, that is, in a direction in which the contour 40 is increased.

Figure 5A:
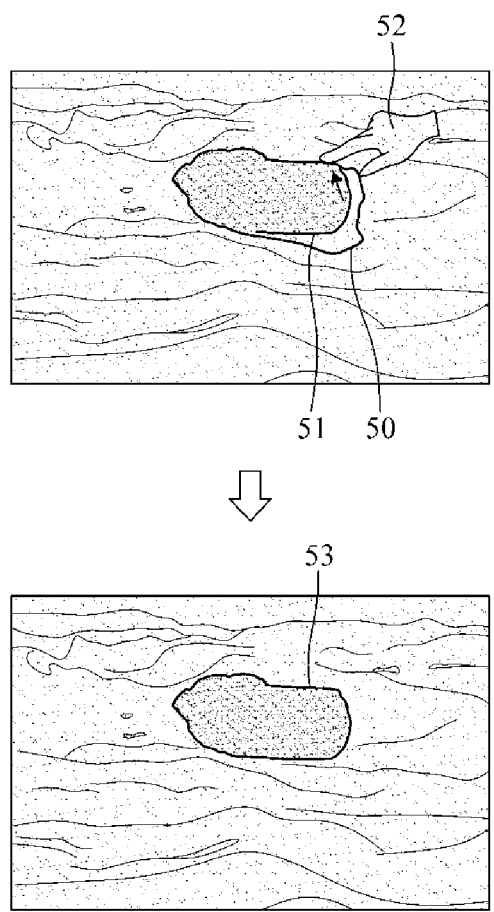
FIGS. 5A to 5B are diagrams illustrating examples of a free modification mode of a contour segmentation apparatus.
Figure 5B:
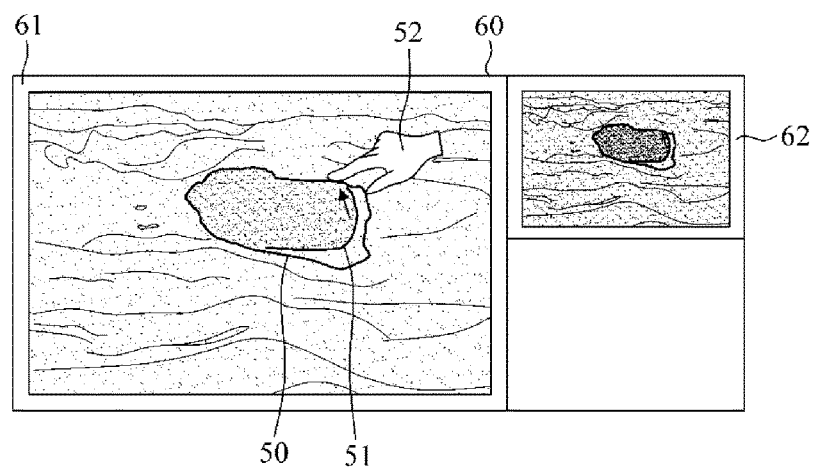

FIGS. 5A to 5B are diagrams illustrating examples of a free modification mode of the contour segmentation apparatus 100. Referring to FIGS. 1 and 5A to 5B, the contour segmentation apparatus 100 supports the free modification mode so that a user may freely modify a contour.

As shown in an upper portion of FIG. 5A, a user directly draws a contour 51 on an interface using an input object 52 with respect to a part to be modified in an original contour 50. The user may partially or wholly modify the original contour 50 in a relatively minute manner. The contour modification unit 130 modifies the original contour 50 based on an operation of the user directly drawing the contour 51. In this manner, a finally-modified contour 53 may be displayed on the interface as shown in FIG. 5B. Meanwhile, the user may modify the contour by repeatedly drawing the contour several times until a user's desired contour is generated and displayed.

Referring to FIG. 5B, when a user draws the contour 51 using the input object 52 so as to modify the original contour 50 output on an image output area 61 of an interface 60, the interface unit 120 may display, on a predetermined area 62 of the interface 60, a part in which the contour 51 is drawn excluding the input object 52. This is to allow the user to confirm that the contour 51 is accurately drawn when the contour 51 is covered by the input object 52 and not visible to the user. The predetermined area 62 may support a magnifying glass mode that may be used by the user to magnify or reduce the part in which the contour 51 is drawn in at least one step (e.g., magnification or demagnification) selected by the user, so that the user may easily confirm that the contour 51 is accurately drawn by magnifying or reducing the part in which the contour 51 is drawn in a stepwise manner.

Figure 6:
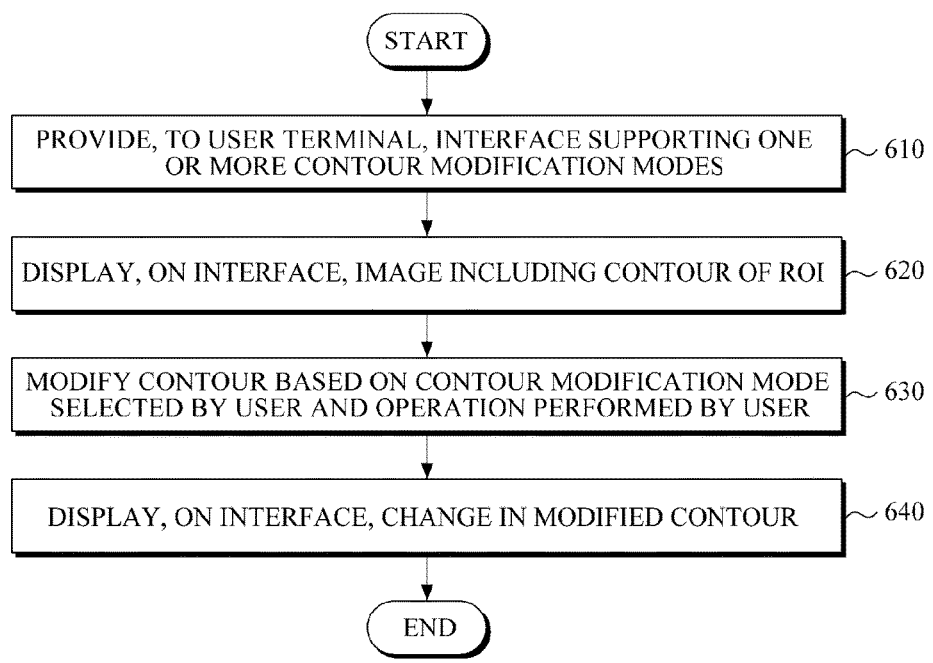
FIG. 6 is a flowchart illustrating an example of a contour segmentation method.

FIG. 6 is a flowchart illustrating an example of a contour segmentation method, and FIG. 7 is a detailed flowchart illustrating an example of modifying of a contour in the contour segmentation method. Referring to FIGS. 6 and 7, the contour segmentation method may be performed by the contour segmentation apparatus 100 of FIG. 1.

In operation 610, the contour segmentation apparatus 100 provides, to a user terminal, an interface supporting one or more contour modification modes. A user may perform a variety of operations on the interface, using a variety of input objects, such as for example, a hand, fingers, a mouse, a stylus, and/or other input objects known to one of ordinary skill in the art. The contour segmentation apparatus 100 may receive and process an input corresponding to an operation performed on the interface by the user. The contour modification modes may include a partial modification mode, an entire modification mode, and/or a free modification mode as shown in FIG. 2, and each of the modes may be output on the contour modification mode selection area 21 of the interface so that the user may select any of the modes.

In operation 620, the contour segmentation apparatus 100 superimposes, on an image, a contour of an ROI extracted from the image, and displays, on the interface, the superimposed image including the contour. The contour segmentation apparatus 100 may receive the image and/or information of the contour from a CAD system or an image processing system, generate the contour based on the received information, superimpose the generated contour on the received image, and display the superimposed contour on the interface. The contour segmentation apparatus 100 may extract the information of the contour from the image when only the image is received.

In operation 630, when the user selects any of the contour modification modes and performs a predetermined operation to modify the contour, the contour segmentation apparatus 100 modifies the contour based on a contour modification mode selected by the user from the contour modification modes, and an input corresponding to the predetermined operation performed by the user. The modifying of the contour will be described in more detail with reference to FIG. 7.

Referring to FIG. 7, in operation 701, the contour segmentation apparatus 100 receives, from the user, the selected contour modification mode and the input corresponding to the predetermined operation In operation 702, the contour segmentation apparatus 100 determines whether the selected contour modification mode is the entire modification mode, the partial modification mode, or the free modification mode. When the selected contour modification mode is determined to be the entire modification mode, the contour segmentation apparatus 100 continues in operation 703. When the selected contour modification mode is determined to be the partial modification mode, the contour segmentation apparatus 100 continues in operation 705. When the selected contour modification mode is determined to be the free modification mode, the contour segmentation apparatus 100 continues in operation 711.

In operation 703, the contour segmentation apparatus 100 adjusts a threshold value and/or a parameter of a contour segmentation algorithm with respect to an entire range of the contour displayed on the interface. The user may confirm a point (for example, a click point, and a start point of panning and dragging operations) where the operation is performed by the user, and determine whether to modify the contour inward or outward. As described above in FIG. 4, when the operation is performed inside the contour, the threshold value may be set to be higher than an original threshold value to thereby reduce the contour, and when the operation is performed outside the contour, the threshold value may be set to be lower than the original threshold value to thereby increase the contour.

In addition, an adjustment width of the threshold value may be adjusted to be different based on a type of an input according to the operation performed by the user, a strength of the input, and/or a speed of the input, whereby a degree of a change in the contour may be changed. As described above, when an operation, such as a repetition of a click operation, a panning operation, and/or a dragging operation, in which a discrete input is performed, the adjustment width of the threshold value may be increased so that the contour may be discretely changed. On the other hand, when a continuous input, such as a pressing operation for a predetermined time is performed, the adjustment width of the threshold value may be reduced so that the contour may be continuously changed.

In operation 704, the contour segmentation apparatus 100 applies the adjusted threshold value and/or parameter to the contour segmentation algorithm to recalculate the entire contour.

In operation 705, the contour segmentation apparatus 100 determines whether a request to set or modify a predetermined range in which the user modifies the contour is received, i.e., whether a range modification is requested. When the range modification is determined to be requested, the contour segmentation apparatus 100 continues in operation 707. Otherwise, the contour segmentation apparatus 100 continues in operation 706.

In operation 706, the contour segmentation apparatus 100 defines a contour modification range as a predetermined-size range with respect to an initial point where the operation is performed.

In operation 707, the contour segmentation apparatus 100 displays or provides, on the interface, a menu that may be used by the user to select a variety of modes that may be used to set the contour modification range on the interface, i.e., range setting modes. For example, the range setting modes may include a range setting mode using figures, a range setting mode using a free region, a range setting mode using a free curved line, as shown in FIGS. 3B to 3D.

In operation 708, when the user sets a predetermined range using a selected range setting mode, the contour segmentation apparatus 100 defines the contour modification range as the predetermined range set directly by the user. When the predetermined-size range or the predetermined range set by the user includes the entire contour displayed on the interface as described above, the entire modification mode may be operated.

In operation 709, the contour segmentation apparatus 100 adjusts the threshold value and/or the parameter with respect to the defined predetermined range. In the same manner as in the entire modification mode, the adjustment width of the threshold value may be adjusted to be different based on the point where the operation is performed by the user within the defined predetermined range, the type of the input according to the operation performed by the user, the strength of the input, and/or the speed of the input, whereby the degree of the change in the contour may be changed.

In operation 710, the contour segmentation apparatus 100 applies the adjusted threshold value and/or the parameter to the contour segmentation algorithm to recalculate the defined predetermined range of the contour.

In operation 711, when the user performs an operation of drawing the contour on the interface, the contour segment apparatus 100 modifies the contour based on the input corresponding to the operation, and displays the contour drawn by the user on the interface.

In operation 712, the contour segmentation apparatus 100 determines whether magnification request is received that allows a part in which the contour is drawn, excluding an input object, to be displayed on a predetermined area of the interface. When the magnification request is determined to be received, the contour segmentation apparatus 100 continues in operation 713. Otherwise, the contour segmentation apparatus 100 ends the contour segmentation method.

In operation 713, the contour segmentation apparatus 100 magnifies and displays the part in which the contour is drawn on the predetermined area of the interface. For example, information of the magnification may be received from the user, and the contour may be magnified and displayed to match the information.

Referring again to FIG. 6, in operation 640, the contour segmentation apparatus 100 displays, on the interface, the change in the modified contour. For example, the change in the modified contour may be displayed by differentiating a type, a color, and/or a thickness of the modified contour from those of an original contour, so that the user may easily confirm the change in the modified contour.

The various units and methods described above may be implemented using one or more hardware components, one or more software components, or a combination of one or more hardware components and one or more software components.

A hardware component may be, for example, a physical device that physically performs one or more operations, but is not limited thereto. Examples of hardware components include microphones, amplifiers, low-pass filters, high-pass filters, band-pass filters, analog-to-digital converters, digital-to-analog converters, and processing devices.

A software component may be implemented, for example, by a processing device controlled by software or instructions to perform one or more operations, but is not limited thereto. A computer, controller, or other control device may cause the processing device to run the software or execute the instructions. One software component may be implemented by one processing device, or two or more software components may be implemented by one processing device, or one software component may be implemented by two or more processing devices, or two or more software components may be implemented by two or more processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

A processing device configured to implement a software component to perform an operation A may include a processor programmed to run software or execute instructions to control the processor to perform operation A. In addition, a processing device configured to implement a software component to perform an operation A, an operation B, and an operation C may include various configurations, such as, for example, a processor configured to implement a software component to perform operations A, B, and C; a first processor configured to implement a software component to perform operation A, and a second processor configured to implement a software component to perform operations B and C; a first processor configured to implement a software component to perform operations A and B, and a second processor configured to implement a software component to perform operation C; a first processor configured to implement a software component to perform operation A, a second processor configured to implement a software component to perform operation B, and a third processor configured to implement a software component to perform operation C; a first processor configured to implement a software component to perform operations A, B, and C, and a second processor configured to implement a software component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

Software or instructions that control a processing device to implement a software component may include a computer program, a piece of code, an instruction, or some combination thereof, that independently or collectively instructs or configures the processing device to perform one or more desired operations. The software or instructions may include machine code that may be directly executed by the processing device, such as machine code produced by a compiler, and/or higher-level code that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

For example, the software or instructions and any associated data, data files, and data structures may be recorded, stored, or fixed in one or more non-transitory computer-readable storage media. A non-transitory computer-readable storage medium may be any data storage device that is capable of storing the software or instructions and any associated data, data files, and data structures so that they can be read by a computer system or processing device. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, or any other non-transitory computer-readable storage medium known to one of ordinary skill in the art.

Functional programs, codes, and code segments that implement the examples disclosed herein can be easily constructed by a programmer skilled in the art to which the examples pertain based on the drawings and their corresponding descriptions as provided herein.

As a non-exhaustive illustration only, a terminal and a device described herein may be a mobile device, such as a cellular phone, a personal digital assistant (PDA), a digital camera, a portable game console, an MP3 player, a portable/personal multimedia player (PMP), a handheld e-book, a portable laptop PC, a global positioning system (GPS) navigation device, a tablet, a sensor, or a stationary device, such as a desktop PC, a high-definition television (HDTV), a DVD player, a Blue-ray player, a set-top box, a home appliance, or any other device known to one of ordinary skill in the art that is capable of wireless communication and/or network communication.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An apparatus for determining a contour of a region of interest (ROI) in a computer-aided diagnosis (CAD) system, comprising:
  a display; and
  at least one processor operatively coupled to the display, wherein the at least one processor is configured to:
    generate a first contour of the ROI from an image by applying a contour segment algorithm having a pre-defined threshold value to the image,
    control the display to display the first contour of the ROI on the image and a plurality of user interfaces (UIs) corresponding to a plurality of modes for modifying the first contour, the plurality of modes comprising a partial modification mode, an entire modification mode and a free modification mode,
    detect a selection of an UI corresponding to the partial modification mode among the plurality of UIs,
    determine an area comprising a part to be modified of the first contour in response to detecting a first input on the image, and
    modify the part of the first contour to a second contour in response to detecting a second input which is different from the first input,
  wherein the at least one processor is further configured to modify the part of the first contour to the second contour by:
    adjusting the pre-defined threshold value of the contour segment algorithm that is used to generate the first contour of the ROI from the image to a first threshold value higher than the pre-defined threshold value in response to detecting the second input inside of the first contour, and applying the contour segment algorithm having the first threshold value to the area such that the part of the first contour is moved inward of the first contour, and
    adjusting the pre-defined threshold value of the contour segment algorithm that is used to generate the first contour of the ROI from the image to a second threshold value lower than the pre-defined threshold value in response to detecting the second input outside of the first contour, and applying the contour segment algorithm having the second threshold value to the area such that the part of the first contour is moved outward of the first contour.

2. The apparatus of claim 1, wherein the at least one processor is further configured to adjust the pre-defined threshold value of the contour segment algorithm based on whether a type of the second input is a discrete input or a continuous input.

3. The apparatus of claim 2, wherein the at least one processor is further configured to:
  modify an adjustment width of the pre-defined threshold value larger than a previous adjustment width of the pre-defined threshold value in response to detecting the discrete input; and
  modify an adjustment width of the pre-defined threshold value smaller than a previous adjustment width of the pre-defined threshold value in response to detecting the continuous input.

4. The apparatus of claim 1, wherein the at least one processor is further configured to:
  control the display to display a predetermined area for modifying the part of the first contour; and
  modify a size of the predetermined area in response to detecting a third input.

5. The apparatus of claim 1, wherein the at least one processor is further configured to:
  control a transceiver of the apparatus to receive data for the ROI from a terminal for extracting the ROI; and
  control the transceiver to transmit data for the second contour to the terminal.

6. The apparatus of claim 1, wherein the at least one processor is further configured to:
  detect a selection of an UI corresponding to the entire modification mode among the plurality of UIs, and
  upon detecting that the entire modification mode is selected, control the display to display a third contour where the entire part of the first contour is modified by applying the contour segment algorithm that the pre-defined threshold value is changed to an entire part of the image.

7. The apparatus of claim 1, wherein the at least one processor is further configured to:
  detect a selection of an UI corresponding to the free modification mode among the plurality of UIs, and
  upon detecting that the free modification mode is selected, control the display to display a forth contour which is generated in response to drawing of the second input.

8. The apparatus of claim 1, wherein the at least one processor is further configured to control the display to display the second contour of which a color, a type, or a thickness is different from a color, a type, or a thickness of the first contour.

9. A method for determining a contour of a region of interest (ROI) in a computer-aided diagnosis (CAD) system, comprising:
  generating a first contour of the ROI from an image by applying a contour segment algorithm having a pre-defined threshold value to the image;
  displaying the first contour of the ROI on the image and a plurality of user interfaces (UIs) corresponding to a plurality of modes for modifying the first contour, the plurality of modes comprising a partial modification mode, an entire modification mode and a free modification mode;

detecting a selection of an UI corresponding to the partial modification mode among the plurality of UIs;
determining an area comprising a part to be modified of the first contour in response to detecting a first input on the image; and
modifying the part of the first contour to a second contour in response to detecting a second input which is different from the first input,
wherein modifying the part of the first contour to the second contour comprises:
   adjusting the pre-defined threshold value of the contour segment algorithm that is used to generate the first contour of the ROI from the image to a first threshold value higher than the pre-defined threshold value in response to detecting the second input inside of the first contour, and applying the contour segment algorithm having the first threshold value to the area such that the part of the first contour is moved inward of the first contour, and
   adjusting the pre-defined threshold value of the contour segment algorithm that is used to generate the first contour of the ROI from the image to a second threshold value lower than the pre-defined threshold value in response to detecting the second input outside of the first contour, and applying the contour segment algorithm having the second threshold value to the area such that the part of the first contour is moved outward of the first contour.

10. The method of claim 9, wherein the pre-defined threshold value of the contour segment algorithm is adjusted based on whether a type of the second input is a discrete input or a continuous input.

11. The method of claim 10, wherein modifying the part of the first contour comprises:
   modifying an adjustment width of the pre-defined threshold value larger than a previous adjustment width of the pre-defined threshold value in response to detecting the discrete input; and
   modifying an adjustment width of the pre-defined threshold value smaller than a previous adjustment width of the pre-defined threshold value in response to detecting the continuous input.

12. The method of claim 9, further comprising:
   displaying a predetermined area for modifying the part of the first contour; and
   modifying a size of the predetermined area in response to detecting a third input.

13. The method of claim 9, further comprising:
   receiving data for the ROI from a terminal for extracting the ROI; and
   transmitting data for the second contour to the terminal.

14. The method of claim 9, further comprising:
   detecting a selection of an UI corresponding to the entire modification mode among the plurality of UIs; and
   upon detecting that the entire modification mode is selected, displaying a third contour where the entire part of the first contour is modified by applying the contour segment algorithm, that the pre-defined threshold value is changed, to an entire part of the image.

15. The method of claim 9, further comprising:
   detecting a selection of an UI corresponding to the free modification mode among the plurality of Ms, and
   upon detecting that the free modification mode is selected, displaying a forth contour which is generated in response to drawing of the second input.

16. The method of claim 9, further comprising displaying the second contour of which a color, a type, or a thickness is different from a color, a type, or a thickness of the first contour.

17. The apparatus of claim 1, wherein the at least one processor is further configured to:
   determine a strength of the second input, and
   adjust the pre-defined threshold value of the contour segment algorithm based on the strength of the second input.

18. The apparatus of claim 1, wherein the at least one processor is further configured to:
   determine a speed of the second input, and
   adjust the pre-defined threshold value of the contour segment algorithm based on the speed of the second input.

19. The method of claim 9, wherein the pre-defined threshold value of the contour segment algorithm is adjusted based on a strength of the second input.

20. The method of claim 9, wherein the pre-defined threshold value of the contour segment algorithm is adjusted based on a speed of the second input.

* * * * *